United States Patent
Mizuochi

(10) Patent No.: US 6,648,472 B1
(45) Date of Patent: Nov. 18, 2003

(54) OPHTHALMIC IMAGING APPARATUS

(75) Inventor: Masaharu Mizuochi, Hamamatsu (JP)

(73) Assignee: Kowa Company Ltd., Aichi (JP)

( * ) Notice: Subject to any disclaimer, the term of this patent is extended or adjusted under 35 U.S.C. 154(b) by 0 days.

(21) Appl. No.: 10/237,395

(22) Filed: Sep. 9, 2002

(51) Int. Cl.$^7$ ................................. A61B 3/14
(52) U.S. Cl. ...................................... 351/206
(58) Field of Search ................. 351/205, 206, 351/221, 211, 212; 396/18

(56) References Cited

U.S. PATENT DOCUMENTS 5,220,360 A * 6/1993 Verdooner et al. .......... 351/212
5,630,179 A * 5/1997 Kishida ....................... 396/18
6,456,787 B1 * 9/2002 Matsumoto et al. .......... 396/18

* cited by examiner

Primary Examiner—George Manuel
(74) Attorney, Agent, or Firm—Adams & Wilks

(57) ABSTRACT

An ophthalmic imaging apparatus has a first storage means that stores image data acquired from an eye being examined. The apparatus further has a second storage means that is slower than the first storage means and is used to hold image data transferred from the first storage means. It is determined whether or not the imaging of the eye is performed in a specific continuous imaging mode. If it is determined that the system is in the continuous imaging mode, the transfer of image data from the first to second storage means is held back until the continuous imaging mode terminates. Otherwise the transfer of image data is carried out for each imaging operation.

10 Claims, 2 Drawing Sheets

OPHTHALMIC IMAGING APPARATUS

BACKGROUND OF THE INVENTION

1. Field of the Invention

The present invention relates to an ophthalmic imaging apparatus, and more particularly to an ophthalmic imaging apparatus comprising a first storage means that stores image data from a subject eye imaged by an electronic imaging means, and a second storage means that is slower than the first storage means and records image data transferred from the first storage means.

2. Description of the Prior Art

A CCD image sensor is an example of the type of electronic imaging device that is used by an ophthalmic imaging apparatus such as an eye fundus camera for obtaining images of an eye being examined. In such an apparatus, the images thus obtained are stored on external storage media such as hard or flexible disks, MO media, memory cards, and so forth. For this purpose, the image data is stored as raw bit-map data or in a compressed data format such as JPEG.

Some such apparatuses use a fluorescent imaging mode to perform continuous imaging. In this mode, a fluorescent agent is injected into the patient's veins to obtain images of the distribution of the fluorescent agent into blood vessels in the eye fundus. To obtain images of the fluorescent agent spreading through the blood vessels of the eye fundus, continuous imaging has to be performed a plurality of times, such as from several times up to several tens of times, within a short period of time ranging from several seconds to several tens of seconds. In most cases, a single image is obtained by pressing the shutter button once, and when the shutter button is kept depressed, continuous imaging is performed providing the images being taken at time intervals determined by hardware operating conditions.

In fluorescent imaging, the fluorescent is injected and this is immediately followed by a start button being pressed to activate a timer that measures the injection timing. The injection timing information is recorded together with the images obtained.

A problem that arises with respect to continuous fluorescent imaging is that of the constraints imposed by the speed of the external storage device to which the image data is written. This imposes limitations on the number of continuous imaging cycles required to accomplish the fluorescent imaging. Another problem is that, when the CCD image data is obtained as color data that is then processed to convert the data to black-and-white images, the data transfer time after imaging tends to increase.

An object of the present invention is to provide an ophthalmic imaging apparatus that enables the number of imaging cycles to be reduced to assure the required number of continuous imaging operations particularly in the case of continuous imaging mode.

SUMMARY OF THE INVENTION

According to the present invention an ophthalmic imaging apparatus comprises a first storage means that stores image data from a subject eye imaged by an electronic imaging means, a second storage means that is slower than the first storage means and records image data transferred from the first storage means, means for determining whether or not the eye is imaged by the electronic imaging means in a specific continuous imaging mode, and means responsive to said determination for controlling transfer timing of image data from the first storage means to the second storage means.

Further features of the invention, its nature and various advantages will be more apparent from the accompanying drawings and following detailed description of the invention.

DESCRIPTION OF THE PREFERRED EMBODIMENT

Figure 1:
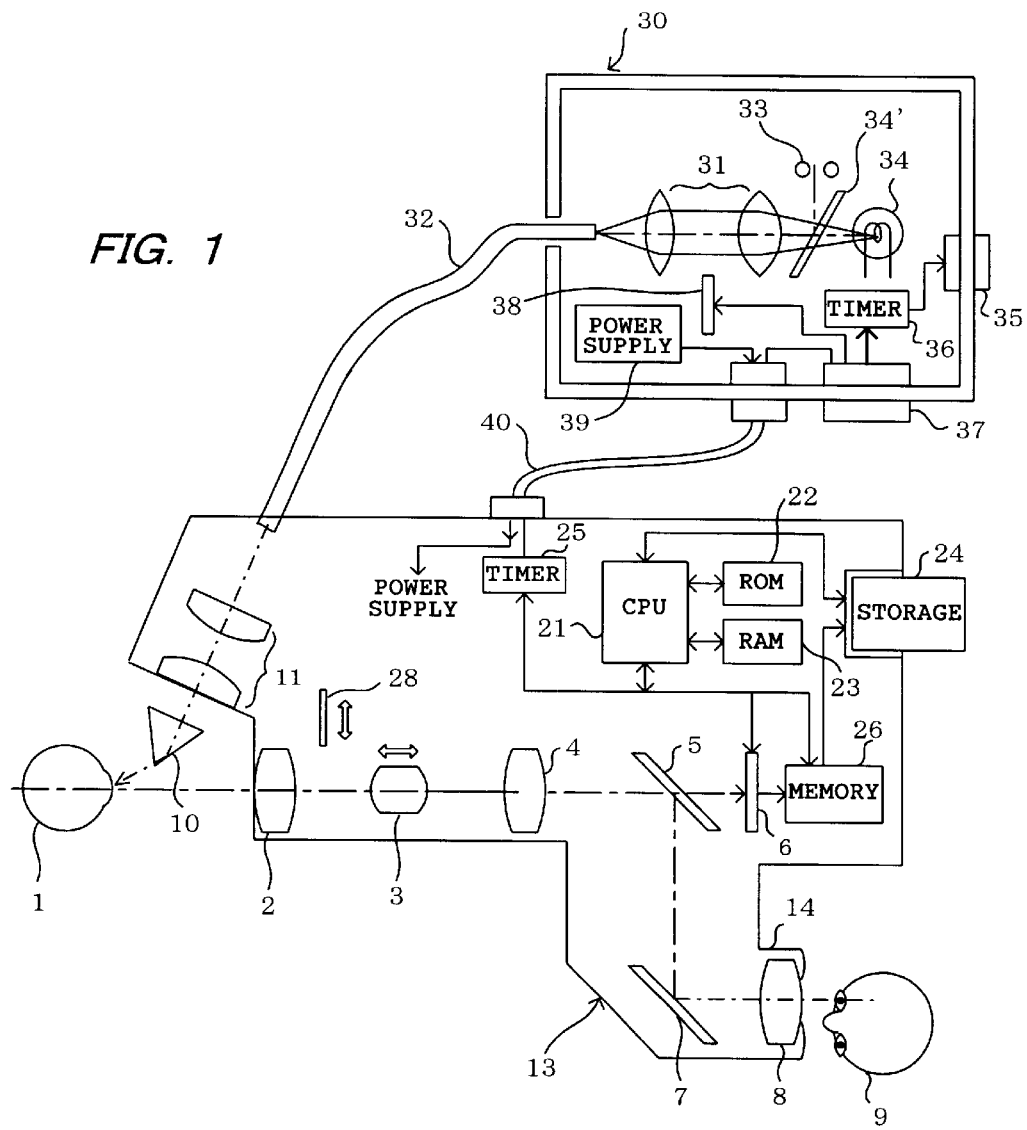
FIG. 1 is an illustrative view for illustrating the arrangement of an ophthalmic imaging apparatus such as an eye fundus camera according to the present invention.

FIG. 1 shows the arrangement of an eye fundus camera constituting the ophthalmic imaging apparatus of the present invention. The eye fundus camera of FIG. 1 comprises a system unit 13 and a power supply unit 30. The power supply unit 30 houses the illumination power supply, the power supply circuitry and part of the control circuitry. First the system unit 13 will be described.

In FIG. 1, images from the fundus of the eye 1 being examined are transmitted to a mirror 5, via an object lens 2, focussing lens 3 and relay lens 4. The mirror 5 is a return mirror which, as shown, is disposed on the optical path to deflect the acquired images through a mirror 7 and ocular lens 8 to a finder 14 for observation by an examiner 9. During imaging operation the mirror 5 is removed from the optical path to allow the eye fundus camera images to be taken by a CCD 6. In this embodiment, the CCD 6 is a color CCD sensor that outputs RGB data. During fluorescent imaging, a barrier filter 28 is inserted between the object lens 2 and the focussing lens 3, or at another such appropriate position. The image data from the CCD 6 is buffered in a memory 26 constituting the first storage memory.

The memory 26 is a semiconductor memory device that has sufficient capacity to hold the number of images required for the continuous fluorescent imaging. In this embodiment, the memory 26 has to have a sufficiently higher-speed input/output capability compared to a lower-speed external storage unit 24 constituting the second storage means. The memory 26 can be comprised of DRAM, SDRAM, DDR SDRAM or other such memory with peripheral circuitry used specifically for storing image data.

In fluorescent imaging, assuming that the memory has sufficient capacity, the number of images taken within a given period depends on the system performance with respect to data transfer from the CCD 6 to the memory 26. If the memory 26 has a good enough I/O performance, the number of continuous fluorescent images can be increased. Image data from the CCD 6 can be stored in the memory 26 as raw bit-map data, or in a compressed format to enables the memory 26 to be utilized more efficiently. The data can be compressed between the CCD 6 and the memory 26 by hardware means or by software under the control of a CPU 21.

The CPU 21 in the system unit 13 provides the control means. The CPU 21 cooperates with a RAM 23 used as working memory, and controls the overall system operation in accordance with a program stored in a ROM 22. The CPU 21 controls the transfer timing of image data from the memory 26 to the external storage unit 24 in accordance with control procedures described below. The external storage unit 24 is comprised by removable media such as flexible or hard disk, MO, memory cards or the like that retain their contents even when the power is switched off. The external storage unit 24 does not have to be removable, and can be controlled as described below, even if it is implemented as a hard-disk type of storage.

The system unit 13 has a timer 25 that is interlocked with a timer 36 in the power supply unit 30. The timer 25 measures time elapsed from the injection of the fluorescent agent into veins in the fluorescent imaging mode. The time thus measured by the timer 25 is imaged as image information by using a character generator (not shown). This time information is superimposed on the image data from the CCD 6 and stored together therewith.

The power supply unit 30 is used to provide power for illumination and to supply power to each part. FIG. 1 shows the power supply unit 30 as being separate from the system unit 13, but it does not have to be separately configured. In particular, the timers 25 and 36 provided in the system unit 13 and power supply unit 30 can be made unitary using just one timer. For illumination, the power supply unit 30 has a flash lamp 33 and a lamp 34. A mirror 34' (a return mirror, or half-mirror) and relay lenses 31 are disposed in front of the flash lamp 33 to direct the light from the lamps 33 and 34 into an optical fiber 32. The end of the optical fiber 32 is guided to the system unit 13 to project the illuminating light towards the eye 1 via lens 11 and an illuminating prism 10. During fluorescent imaging, an exciter filter 38 is inserted into the optical system between the lenses 31 to provide fluorescent illumination.

A power supply circuit 39 in the power supply unit 30 supplies power to each part in the power supply unit 30 and, via a cable 40, also supplies power to each part in the system unit 13. As described above, the power supply unit 30 has the timer 36 that is interlocked with the timer 25 in the system unit 13. Like the timer 25, the timer 36 measures time elapsed from the time the fluorescent agent is injected into the patient's veins.

A display unit 35 and an operation section 37 form the user interface via which the examiner 9 controls the imaging. The display unit 35 and operation section 37 are provided on the side of the power supply unit 30, but may instead be provided on the side of the system unit 13. The examiner 9 uses the operation section 37 to set whether the system performs fluorescent imaging or another type of imaging such as imaging using visible light or infrared light. The operation section 37 also includes start buttons for starting the timers 25 and 36 used to measure elapsed time from the venous injection. If necessary, conditions set via the operation section 37 can be displayed on the display unit 35. During the imaging, the display unit 35 can also be used to monitor system status. In the fluorescent imaging mode, the time elapsed since injection, as measured by the timer 36 (or the timer 25), can be displayed by the display unit 35.

The operation of the system thus configured will now be described.

Figure 2:
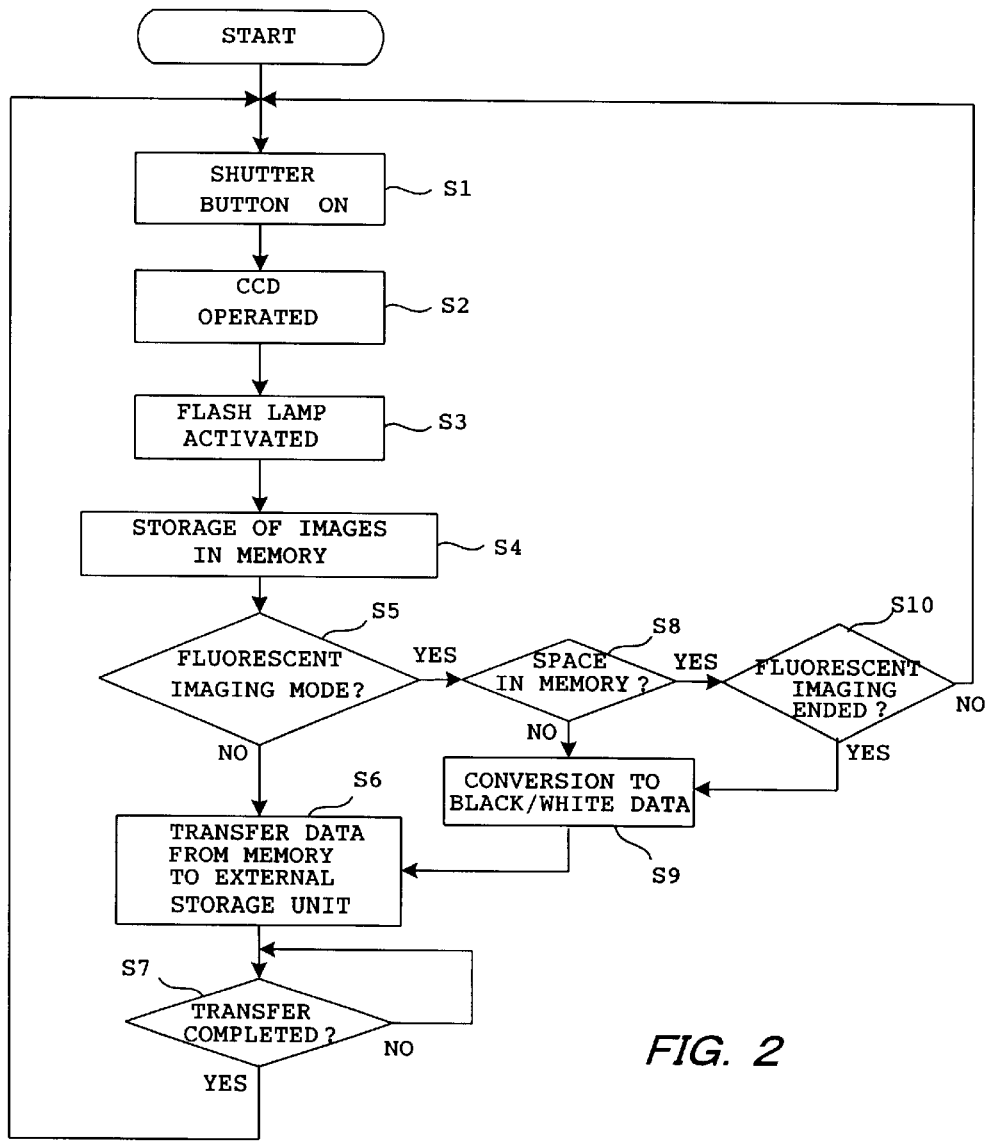
FIG. 2 is a flow chart for illustrating control procedures of the CPU used in the ophthalmic imaging apparatus as shown in FIG. 1.

FIG. 2 shows the control process that the CPU 21 uses to control the imaging in accordance with a program stored in the ROM 22 or in other storage media. The operation section 37 is used to select imaging modes such as fluorescent imaging mode, visible light or infrared light imaging mode prior to the start of the control sequence of FIG. 2. Then, the examiner 9 injects the patient with the fluorescent agent and uses the start button on the operation section 37 to start the timers 25 and 36 before initiating the imaging.

In step S1 of FIG. 2, the system detects whether the examiner 9 has operated the shutter button (not shown) for producing the imaging command. If the imaging timing has been reached in step S1, the CCD 6 is made active in step S2 to initiate the imaging. In step S2, the associated mirrors are controlled for movement into predetermined positions and the barrier filter 28 and exciter filter 38 are inserted into, or retracted from, the optical path, in accordance with whether the mode is set for fluorescent imaging or non-fluorescent imaging.

In step S3, the flash lamp 33 is activated, and in step S4 the image data from the CCD 6 is stored in the memory 26. In the fluorescent imaging mode, a plurality of images are stored sequentially in the memory 26 in a format that enables each image to be identified. In step S5, it is determined whether or not the system is set to the fluorescent imaging mode. If it is determined that the system is not set to the fluorescent imaging mode, system operation moves to step S6. If it is determined that the system is set to the fluorescent imaging mode, the system moves to step S8. The determination of which mode the system is in is based on settings input by the user via the operation section 37 (system flags and the like signifying the imaging mode), and can also be based on the following conditions.

(1) Whether the barrier filter 28 and exciter filter 38 are inserted or not. The system detects that the system is in the fluorescent imaging mode when these filters are inserted, and detects that the system is not in the fluorescent imaging mode when the filters are not inserted. Such detection is useful in a system in which the filters used for the fluorescent imaging are directly controlled manually without carrying out detailed settings via the operation section 37.

(2) The operational status of the timers 25 and 36 used to measure elapsed time from the injection of the fluorescent agent. The system detects that the mode is fluorescent imaging mode if the timers are in operation, while if the timers are not in operation, the system detects that the system is not in fluorescent imaging mode.

The above conditions (1) and (2) can be independently applied, or the logical sum of the two conditions can be applied. For example, the system can be constructed in such a way that it is only determined that the system is in the fluorescent imaging mode when both conditions apply.

In step S6, the acquired image data in the memory 26 is transferred to the external storage unit 24. If the system is in a non-fluorescent imaging mode, or in a fluorescent imaging mode in which the memory 26 does not have sufficient capacity, an amount of data corresponding to one image is transferred to the external storage unit 24 in step S6 for each imaging process. In other fluorescent imaging modes, an amount of data corresponding to a plurality of images is transferred in step S6 to the external storage unit 24 upon completion of the fluorescent imaging mode.

In step S7, the system waits for the transfer of image data to the external storage unit 24 to end, and then returns to step S1.

In fluorescent imaging mode, the memory 26 stores a plurality of images sequentially. It is determined in step S8 whether or not the memory 26 still has capacity enough to store the amount of data corresponding to at least one image of standard size. If it is determined that the memory 26 does have such enough capacity, the system moves on to step S10, while if it is determined that the memory 26 does not have enough capacity, the system moves to step S9.

In step S9, data in the memory 26 corresponding to one to a plurality of images is converted to black-and-white image data, and the system then moves to step S6, in which image data acquired during fluorescent imaging is stored in the external storage unit 24 as black-and-white image data. The conversion to black-and-white image data in step S9 is performed using RAM 23. However, if the memory 26 is used for the conversion, it is necessary in the capacity determination in step S8 to allow for space that is required for the black-and-white conversion.

In step S10, it is determined whether or not fluorescent imaging has been completed. The termination of the fluorescent imaging can be specified manually by the examiner 9, or, if the fluorescent imaging is being performed automatically, the system can be programmed to determine that imaging is completed when a set number of images have been acquired. If in step S10 it is determined that the imaging has ended, the system moves to step S9. This causes image data in memory 26 to be converted to black-and-white image data and the converted data is then transferred to the external storage unit 24 in step S6.

The image data is converted to a format such as JPEG, GIF or TIFF or the like for storage as a data file in the file system of the external storage unit 24. In the above procedure, the image data is stored in the external storage unit 24 after conversion to black-and-white image data. However, it may not be essential to carry out this conversion process. For example, it would not be necessary if the CCD 6 outputs black-and-white image data.

As described in the foregoing, acquired image data is transferred to the external storage unit 24 one image at a time in non-fluorescent imaging mode or in fluorescent imaging mode with insufficient storage capacity detected, while in the fluorescent imaging mode with sufficient capacity detected, as many images as possible are stored in the memory 26, and they are transferred from the memory 26 to the external storage unit 24 when one continuous imaging sequence has been completed. Since the memory 26 is faster than the external storage unit 24, the transfer of the image data to the external storage unit 24 in the fluorescent imaging mode can be held back. This allows imaging intervals to be reduced, thereby making it possible to achieve a major improvement in performance with respect to the number of images acquired within a set time period. Furthermore, it is possible in the fluorescent imaging mode to reduce the imaging interval because the color images acquired in the fluorescent imaging mode are converted to black-and-white images directly prior to the transfer of the image data to the external storage unit 24. This also provides a major improvement in performance with respect to the number of images acquired within a set time period.

According to the control procedure shown in FIG. 2, the capacity of the memory 26 is monitored in fluorescent imaging mode and, when the capacity is found to be insufficient, image data is transferred from the memory 26 to the external storage unit 24. This makes it possible to avoid problems caused in the fluorescent imaging mode.

Also, according to the control procedure shown in FIG. 2, the transfer of one image of data is carried out in step 6 when the system is in the fluorescent imaging mode and the memory 26 is determined to have insufficient capacity (step S8). This means that, when the memory 26 does not have enough capacity, the image data that is transferred to the external storage unit 24 is limited to the data of one image for each imaging process. This makes it possible to prevent a major deterioration in the image data transfer rate, or the irregular imaging intervals during fluorescent imaging, or other such problems. In this situation, so far as imaging intervals are not extended remarkably, the data of two or more images may be transferred to the external storage unit 24 when the capacity of the memory 26 is determined to be insufficient.

The foregoing has been described with reference to an example in which the transfer of data from the memory 26 to the external storage unit 24 is controlled in accordance with a determination as to whether the system is or is not in fluorescent imaging mode. However, the data transfer can also be carried out depending on whether the imaging is continuous or not. That is, in a specific continuous imaging mode, transfer of the image data from a first storage means (memory 26, in the case of the above-described embodiment) to a second storage means (external storage unit 24, in the above embodiment) that is slower than the first storage means is held back until imaging in the continuous imaging mode has ended. This makes it possible to reduce the imaging interval in continuous imaging mode, enabling a major improvement in performance with respect to the number of images acquired within a set time period.

The "specific continuous imaging mode" referred to in the foregoing can apply to a number of modes. For example, when the shutter button is depressed for longer than a prescribed time in step S5 (FIG. 2), it is determined that the specific continuous imaging mode has been established. Or, the specific continuous imaging mode can be determined as having been established when the operation section 37 is used to select a specific imaging program that is executed to continuously acquire a set number of images in a predetermined imaging interval.

As described in the foregoing, the ophthalmic imaging apparatus of the present invention comprises a first storage means that stores image data from a subject eye imaged by an electronic imaging means, a second storage means that is slower than the first storage means and records image data transferred from the first storage means, means for determining whether or not the eye is imaged by the electronic imaging means in a specific continuous imaging mode, and means responsive to said determination for controlling transfer timing of image data from the first storage means to the second storage means. Such an arrangement enables the number of imaging cycles to be reduced, particularly in the case of continuous imaging modes such as fluorescent imaging.

What is claimed is:

1. An ophthalmic imaging apparatus comprising:
    a first storage means that stores image data from a subject eye imaged by an electronic imaging means;
    a second storage means that is slower than the first storage means and records image data transferred from the first storage means;
    means for determining whether or not the eye is imaged by the electronic imaging means in a specific continuous imaging mode; and
    means responsive to said determination for controlling transfer timing of image data from the first storage means to the second storage means.

2. An ophthalmic imaging apparatus according to claim 1, wherein, when imaging is being conducted in the specific continuous imaging mode, image data is not transferred from the first storage means to the second storage means but is only stored in the first storage means, and the image data is transferred from the first storage means to the second storage means upon completion of imaging in said continuous imaging mode.

3. An ophthalmic imaging apparatus according to claim 1, wherein, when imaging is carried out in a mode other than the specific continuous imaging mode, image data is first stored in the first storage means and image data therein is then transferred to the second storage means for each imaging operation.

4. An ophthalmic imaging apparatus according to claim 1, wherein, when imaging is carried out in the specific continuous imaging mode, image data is first stored in the first storage means and image data therein is then transferred to the second storage means for each imaging operation in case where the first storage means has insufficient storage capacity.

5. An ophthalmic imaging apparatus according to claim 1, wherein the specific continuous imaging mode is a fluorescent imaging mode.

6. An ophthalmic imaging apparatus according to claim 5, wherein the state of insertion of filters required for fluorescent imaging into the optical system is used for determination as to whether the imaging mode is the specific continuous imaging mode.

7. An ophthalmic imaging apparatus according to claim 5, wherein the operational state of a timer that measures elapsed time from injection of a fluorescent agent by an examiner is used for determination as to whether the imaging mode is the specific continuous imaging mode.

8. An ophthalmic imaging apparatus according to claim 5, wherein, in fluorescent imaging mode, color image data stored in the first storage means is converted to black-and-white image data and transferred to the second storage means.

9. An ophthalmic imaging apparatus according to claim 1, wherein the second storage means is a storage medium that retains its contents even when its power supply is interrupted.

10. An ophthalmic imaging apparatus according to claim 1, wherein the second storage means is a removable storage medium.

* * * * *